(12) United States Patent
Steffan et al.

(10) Patent No.: US 7,590,309 B1
(45) Date of Patent: Sep. 15, 2009

(54) IMAGE PROCESSING IN INTEGRATED CIRCUIT TECHNOLOGY DEVELOPMENT

(75) Inventors: Paul J. Steffan, Elk Grove, CA (US); Jeffrey P. Erhardt, San Jose, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 1011 days.

(21) Appl. No.: 10/974,381

(22) Filed: Oct. 26, 2004

(51) Int. Cl.
*G06K 9/54* (2006.01)
*G06K 9/60* (2006.01)

(52) U.S. Cl. ...................................................... 382/305

(58) Field of Classification Search ................. 382/305, 382/190–195, 199, 181, 224–228, 141–152, 382/159; 348/125–126, 129–134; 700/121, 700/212, 164–166, 109–115, 204; 707/1–7, 707/104.1; 702/81

See application file for complete search history.

(56) References Cited

U.S. PATENT DOCUMENTS

| 6,456,899 | B1 * | 9/2002 | Gleason et al. ............. 700/212 |
| 6,845,176 | B1 * | 1/2005 | Sezan ......................... 382/168 |
| 7,263,451 | B1 * | 8/2007 | Erhardt et al. ................ 702/81 |

* cited by examiner

*Primary Examiner*—Sherali Ishrat
(74) *Attorney, Agent, or Firm*—Farjami & Farjami LLP

(57) ABSTRACT

An image processing system provides a method for processing an image including classifying the image, comparing the image to stored images, storing the image if the image does not match one of the stored images, and storing a link to a stored image if the image matches one of the stored images.

9 Claims, 2 Drawing Sheets

IMAGE PROCESSING IN INTEGRATED CIRCUIT TECHNOLOGY DEVELOPMENT

BACKGROUND

1. Technical Field

The present invention relates generally to semiconductor technology and more specifically to semiconductor research and development.

2. Background Art

Electronic products are used in almost every aspect of life, and the heart of these electronic products is the integrated circuit. Integrated circuits are used in everything from automobiles to televisions.

Integrated circuits are made in and on silicon wafers by extremely complex systems that require the coordination of hundreds or even thousands of precisely controlled processes to produce a finished semiconductor wafer. Each finished semiconductor wafer has hundreds to tens of thousands of integrated circuits, each worth hundreds or thousands of dollars.

The ideal would be to have every one of the integrated circuits on a wafer functional and within specifications, but because of the sheer numbers of processes and minute variations in the processes, this rarely occurs. "Yield" is the measure of how many "good" integrated circuits there are on a wafer divided by the total number of integrated circuits formed on the wafer divided by the maximum number of possible good integrated circuits on the wafer. A 100% yield is extremely difficult to obtain because minor variations, due to such factors as timing, temperature, and materials, substantially affect a process. Further, one process often affects a number of other processes, often in unpredictable ways.

In a manufacturing environment, the primary purpose of experimentation is to increase the yield. Experiments are performed in-line and at the end of the production line with both production wafers and experimental wafers. However, yield enhancement methodologies in the manufacturing environment produce an abundance of very detailed data for a large number of wafers on processes subject only to minor variations. Major variations in the processes are not possible because of the time and cost of using production equipment and production wafers. Setup times for equipment and processing time can range from weeks to months, and processed wafers can each contain hundreds of thousands of dollars worth of integrated circuits.

The learning cycle for the improvement of systems and processes requires coming up with an idea, formulating a test(s) of the idea, testing the idea to obtain data, studying the data to determine the correctness of the idea, and developing new ideas based on the correctness of the first idea. The faster the correctness of ideas can be determined, the faster new ideas can be developed. Unfortunately, the manufacturing environment provides a slow learning cycle because of manufacturing time and cost.

Recently, the great increase in the complexity of integrated circuit manufacturing processes and the decrease in time between new product conception and market introduction have both created the need for speeding up the learning cycle.

This has been accomplished in part by the unique development of the integrated circuit research and development environment. In this environment, the learning cycle has been greatly speeded up and innovative techniques have been developed that have been extrapolated to high volume manufacturing facilities.

To speed up the learning cycle, processes are speeded up and major variations are made to many processes, but only a few wafers are processed to reduce cost. The research and development environment has resulted in the generation of tremendous amounts of data and analysis for all the different processes and variations. This, in turn, has required a large number of engineers to do the analysis. With more data, the answer always has been to hire more engineers.

However, this is not an acceptable solution for major problems.

The problems include, but are not limited to, the storage of image files consumes large amounts of data storage capability in databases.

Solutions to these problems have been long sought but prior developments have not taught or suggested any solutions and, thus, solutions to these problems have long eluded those skilled in the art.

DISCLOSURE OF THE INVENTION

The present invention provides an image processing system and method for processing an image including classifying the image, comparing the image to stored images, storing the image if the image does not match one of the stored images, and storing a link to a stored image if the image matches one of the stored images.

The present invention enhances the storage capability of image files in databases.

Certain embodiments of the invention have other advantages in addition to or in place of those mentioned above. The advantages will become apparent to those skilled in the art from a reading of the following detailed description when taken with reference to the accompanying drawings.

DETAILED DESCRIPTION OF THE INVENTION

Figure 1:
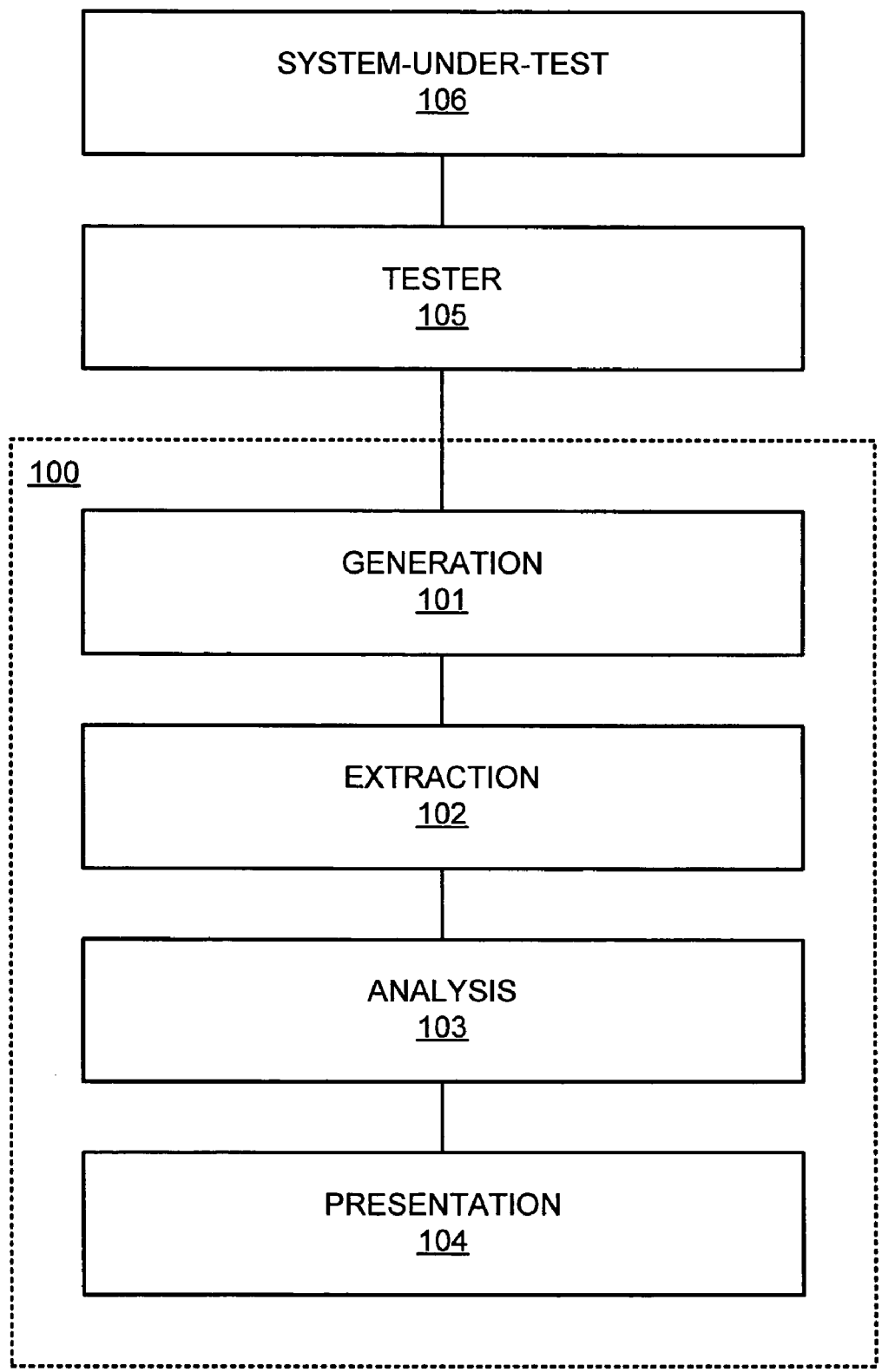
FIG. 1 is a block diagram of a tester information processing system according to the present invention.

Referring now to FIG. 1 therein is shown a block diagram of a tester information processing system 100 according to the present invention. The tester information processing system 100 is the result of the discovery that at times a single fundamental block can solve the problems presented but often there are four fundamental blocks to solving the problems presented.

The four fundamental blocks are a generation block 101, an extraction block 102, an analysis block 103, and a presentation block 104. Each of the blocks can stand independently in the tester information processing system 100, and within these blocks are various commercially available techniques, methodologies, processes, and approaches as well as the invention disclosed herein. The four fundamental blocks are discussed in the approximate chronology that the blocks are used in the tester information processing system 100.

The tester information processing system 100 includes various pieces of commercially available production, test, research, and development semiconductor equipment, which operate on and manipulate information and/or data, which are generically defined herein as "information." The tester information processing system receives information from a tester 105, which is connected to a system-under-test 106.

In the integrated circuit field, the tester 105 can be a semiconductor test system for testing wafers or die and the systemunder-test 106 can be anything from a complete wafer down to an element of an individual semiconductor device on a die.

In the generation block 101, basic information is generated looking at new and old products, new and old processes, product and process problems, unexpected or unpredictable results and variations, etc. Generation of the information may use the tester 105 itself, conventional test information, a personal computer, etc. It may also require new equipment and/or methods, which are described herein when required.

In the extraction block 102, usable information is extracted from the generated information from the generation block 101. Essentially, the generated information is translated into more useful forms; e.g., broken apart so it can be reassembled in different forms to show different inter-relationships.

For example, most testing equipment provides raw data in massive test files. Sometimes, millions of measurements provide millions of pieces of information, which must be digested and understood. The test files seldom have a user-friendly tabular output of parameter and value. Even where somewhat user-friendly outputs are provided, there are problems with the proper schema for storing the usable data and for formatting the data for subsequent analysis.

Extraction of the usable information may also require new equipment and/or methods. Sometimes, extraction includes storing the information for long duration experiments or for different experiments, which are described herein when required.

In the analysis block 103, the usable information from the extraction block 102 is analyzed. Unlike previous systems where a few experiments were performed and/or a relatively few data points determined, the sheer volume of experiments and data precludes easy analysis of trends in the data or the ability to make predictions based on the data. Analysis of the extracted information may also require new equipment and/or methods, which are described herein when required.

In the presentation block 104, the analyzed information from the analysis block 103 is manipulated and presented in a comprehensible form to assist others in understanding the significance of the analyzed data. The huge amount of analyzed information often leads to esoteric presentations, which are not useful per se, misleading, or boring. Proper presentation often is an essential ingredient for making informed decisions on how to proceed to achieve yield and processing improvements. In some cases, problems cannot even be recognized unless the information is presented in an easily understood and digested form, and this often requires new methods of presentation, which are described herein when required.

Figure 2:
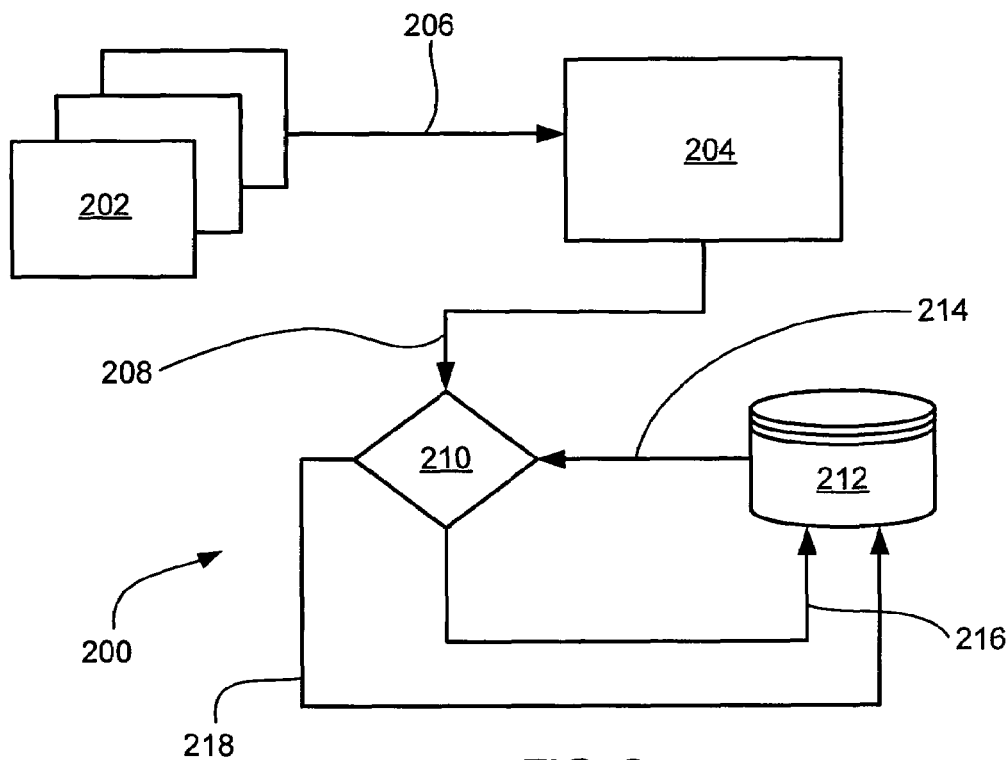
FIG. 2 is a flow diagram of a method of processing image files according to the present invention.

Referring now to FIG. 2 therein is shown a flow diagram of an image storing system 200 for storing and retrieving image files according to the present invention. A number of images 202 are created by the tester 105 shown in FIG. 1, such as images of defects on a semiconductor, or other type of the system under test 106. The images 202 are sent to an image classifier 204 by way of a first data communication link 206. The images 202, in the case of a semiconductor wafer being the system under test 106 shown in FIG. 1, typically show a pattern resembling a semiconductor wafer having small irregularities, such as small black dots representing defects on the semiconductor wafer.

The image classifier 204 typically is able to categorize images based on a large number of descriptive components extracted from the number of images 202. The number of descriptive components can, for example, range upwards of several hundred.

The image classifier 204 categorizes the number of images 202 using a number of descriptive components extracted from the images 202 to create a number of categorized images representative of the number of images 202. The number of categorized images is sent to an image comparator 210 by way of a second data communication link 208.

The image comparator 210 compares the categorized images with an existing library of categorized images stored in a database 212 in accordance with the analysis block 103 shown in FIG. 1. The library of categorized images stored in the database 212 is sent to the image comparator 210 by way of a third data communication link 214. The categorized images representative of the number of images 202 are stored depending upon the results of the comparisons performed by the image comparator 210.

With a database containing up to one million images or more many cannot be distinguished from one another. And the situation is becoming worse. For example, a bitmap for a 128 MB semiconductor memory can require as much as 27 bytes to identify a particular bit address. If the semiconductor memory contains one KB of failed bits scattered across the chip, 27 KB of memory capacity will be required to record the bitmap. For a wafer having 260 chips, this then requires 675 KB, and for one lot of 50 wafers, 33 MB of memory capacity will be required. As information accumulates for many lots over time, the database becomes enormous.

It has been discovered that when the comparison performed by the image comparator 210 results in a high degree of similarity between one of the number of images 202 and one of the images stored in the in the database 212 it is difficult to differentiate the two similar images. For example, if there is a ninety percent (90%) or more similarity between the images, it is difficult to differentiate the new image, as one of the number of images 202, from the matched image from the database 212. It will be apparent to those skilled in the art based on the present disclosure that although ninety percent (90%) similarity has been disclosed herein, varying degrees of similarity may be used depending upon the nature of the system under test 106.

It has been discovered that in a manufacturing environment, such as in a semiconductor manufacturing wafer fabrication facility, it is unnecessary to store image data that does not contain new or additional information.

Accordingly, the number of images 202 is stored in the database 212 based upon the result of the comparison by the image comparator 210. If one of the number of images 202 does not match one of the images stored in the database 212, it is stored as an image 216 in the database 212.

If, on the other hand, one of the number of images 202 matches one of the images stored in the database 212, a link 218 to the matched image already stored in the database 212 is stored instead of saving the new image, and the new image is discarded. The link 218 to the image already in the database consumes virtually no storage space in the database 212.

In the future, when reference to the new image is required, the link 218 retrieves the matched image that already was stored in the database 212 for presentation of the image in accordance with the presentation block 104 shown in FIG. 1. The image storage capability of the database is greatly increased without significant loss of data information.

Figure 3:
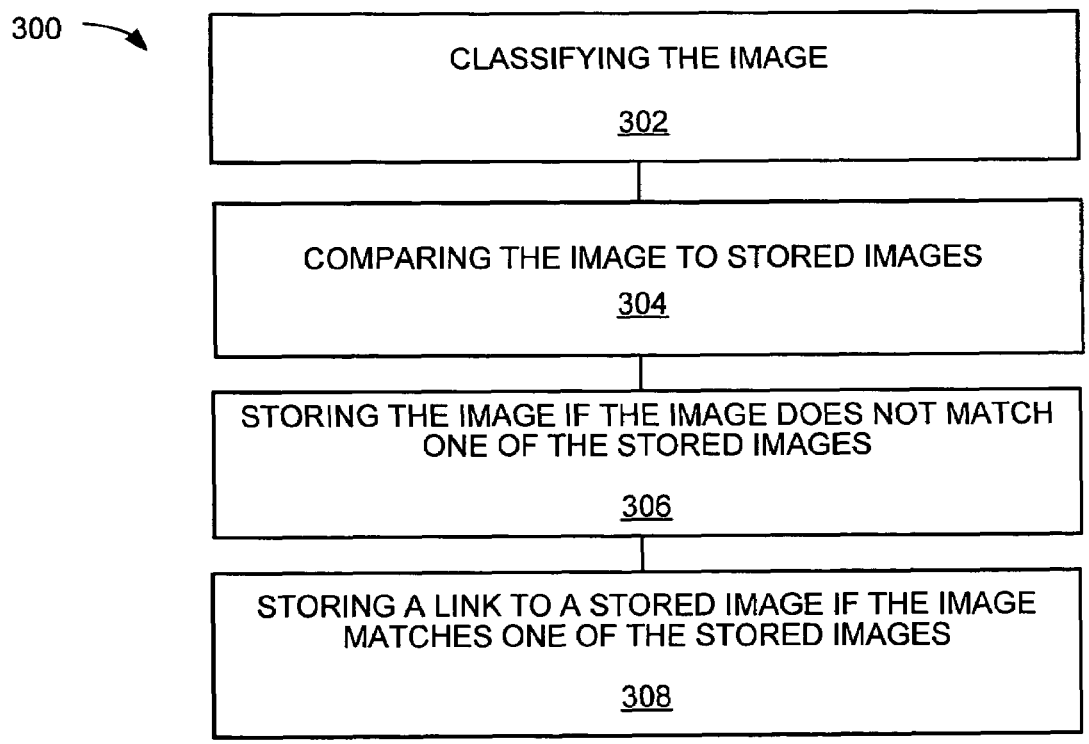
FIG. 3 is a flow chart of a method of the present invention.

Referring now to FIG. 3 therein is shown a flow chart of a method 300 for processing an image in accordance with the present invention. The method 300 includes a step 302 of classifying the image; a step 304 of comparing the image to stored images; a step 306 of storing the image if the image does not match one of the stored images; and a step 308 of storing a link to a stored image if the image matches one of the stored images.

While the invention has been described in conjunction with a specific best mode, it is to be understood that many alternatives, modifications, and variations will be apparent to those skilled in the art in light of the foregoing description. Accordingly, it is intended to embrace all such alternatives, modifications, and variations that fall within the scope of the included claims. All matters hither-to-fore set forth or shown in the accompanying drawings are to be interpreted in an illustrative and non-limiting sense.

The invention claimed:

1. A method for use by an image processing system for processing an image, the method comprising:
   classifying the image by an image classifier of said image processing system;
   comparing the image to stored images in a database of said image processing system, by an image comparator of said image processing system;
   storing the image in said database if the image does not match one of the stored images; and
   storing a link to a matched image already stored in said database if the image matches one of the stored images.

2. The method for processing an image as claimed in claim 1 wherein classifying the image classifies an image of semiconductor manufacturing defects.

3. The method for processing an image as claimed in claim 1 wherein storing a link to the matched image stores a link if the image is at least ninety percent identical to the matched image.

4. The method for processing an image as claimed in claim 1 wherein:
   classifying the image comprises extracting a first number of descriptive components of the image; and
   comparing the image to stored images comprises comparing the first number of descriptive components of the image to stored images having a second number of descriptive components.

5. A system for processing an image comprising:
   an image classifier;
   a database of stored images
   an image comparator;
   means for storing the image in the database if said image does not match one of the stored images in the database; and
   means for storing a link to a matched image already stored in said database if the image matches the stored image.

6. The system for processing an image as claimed in claim 5, wherein the image classifier classifies an image of semiconductor manufacturing defects.

7. The system for processing an image as claimed in claim 5 wherein the image comparator compares the image to stored images in said database.

8. The system for processing an image as claimed in claim 5, wherein the means for storing a link to the matched image stores a link if the image is at least ninety percent identical to the matched image.

9. The system for processing an image as claimed in claim 5 wherein:
   the image classifier extracts a first number of descriptive components of the image; and
   the image comparator compares the first number of descriptive components of the image to stored images having a second number of descriptive components.

\* \* \* \* \*